(12) United States Patent
Yoon et al.

(10) Patent No.: US 10,448,812 B2
(45) Date of Patent: Oct. 22, 2019

(54) SURGICAL TROCARS AND IMAGE ACQUISITION METHOD USING THE SAME

(71) Applicant: Samsung Electronics Co., Ltd., Suwon-Si, Gyeonggi-Do (KR)

(72) Inventors: Suk June Yoon, Seoul (KR); Kyung Shik Roh, Seongnam-si (KR); Soon Yong Park, Bucheon-si (KR); Sung Hwan Ahn, Seongnam-si (KR); Ji Hyo Lee, Suwon-si (KR); Won Jun Hwang, Seoul (KR); Hyo Seok Hwang, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1054 days.

(21) Appl. No.: 14/153,396

(22) Filed: Jan. 13, 2014

(65) Prior Publication Data

US 2014/0330077 A1    Nov. 6, 2014

(30) Foreign Application Priority Data

May 2, 2013    (KR) .................. 10-2013-0049257

(51) Int. Cl.
*A61B 1/00* (2006.01)
*A61B 1/04* (2006.01)
(Continued)

(52) U.S. Cl.
CPC ........ *A61B 1/00183* (2013.01); *A61B 1/0008* (2013.01); *A61B 1/018* (2013.01); *A61B 1/05* (2013.01); *A61B 17/3423* (2013.01); *A61B 17/34* (2013.01); *A61B 17/3415* (2013.01); *A61B 17/3417* (2013.01); *A61B 17/3421* (2013.01); *A61B 90/361* (2016.02); *A61B 90/57* (2016.02); *A61B 2017/00283* (2013.01); (Continued)

(58) Field of Classification Search
CPC .... A61M 2039/0279; A61M 2025/028; A61B 17/34; A61B 17/3421; A61B 17/3417; A61B 17/3423; A61B 1/00174; A61B 1/00183; A61B 1/05; A61B 2017/3445; A61B 17/3415
USPC ................ 600/109, 112, 170–171, 173, 204; 604/506, 164.01, 164.04, 19
See application file for complete search history.

(56) References Cited

U.S. PATENT DOCUMENTS 7,374,533 B2 * 5/2008 Hoeg ................. A61B 1/00183
600/128
8,439,830 B2 * 5/2013 McKinley .......... A61B 17/3421
600/129
(Continued)

FOREIGN PATENT DOCUMENTS

| KR | 20110104234 A | 9/2011 |
| KR | 101150350 B1 | 6/2012 |
| KR | 20120063858 A | 6/2012 |

OTHER PUBLICATIONS

Korean Office Action dated Jul. 17, 2019 for KR Application No. 10-2013-0049257.

*Primary Examiner* — Aaron B Fairchild
(74) *Attorney, Agent, or Firm* — Harness, Dickey & Pierce, P.L.C.

(57) ABSTRACT

Surgical trocars, and image acquisition method using the same, include a body having a passage configured to receive at least one surgical instrument, and at least one camera movably coupled to an outer wall of the body.

14 Claims, 11 Drawing Sheets

(51) Int. Cl.
*A61B 1/018* (2006.01)
*A61B 1/05* (2006.01)
*A61B 17/34* (2006.01)
*A61M 39/02* (2006.01)
*A61M 25/02* (2006.01)
*A61B 17/00* (2006.01)
*A61B 90/57* (2016.01)
*A61B 90/00* (2016.01)

(52) U.S. Cl.
CPC ............. *A61B 2017/3445* (2013.01); *A61M 2025/028* (2013.01); *A61M 2039/0279* (2013.01)

(56) References Cited

U.S. PATENT DOCUMENTS

| | | | | |
|---|---|---|---|---|
| 8,602,980 | B2* | 12/2013 | Bassan | A61B 1/00009 600/129 |
| 8,834,358 | B2* | 9/2014 | Mckinley | A61B 17/3421 600/117 |
| 9,060,678 | B2* | 6/2015 | Larkin | A61B 1/00087 |
| 9,271,637 | B2* | 3/2016 | Farr | A61B 1/00096 |
| 9,307,894 | B2* | 4/2016 | von Grunberg | A61B 1/00064 |
| 2002/0049367 | A1* | 4/2002 | Irion | A61B 1/00183 600/173 |
| 2003/0144649 | A1* | 7/2003 | Ghodoussi | G06F 19/3418 606/1 |
| 2003/0187426 | A1* | 10/2003 | Wang | A61B 34/77 606/1 |
| 2003/0195661 | A1* | 10/2003 | Wang | A61B 34/77 700/258 |
| 2005/0014994 | A1* | 1/2005 | Fowler | A61B 1/00149 600/102 |
| 2005/0165449 | A1* | 7/2005 | Cadeddu | A61B 17/0469 606/232 |
| 2006/0252994 | A1* | 11/2006 | Ratnakar | A61B 1/00179 600/173 |
| 2007/0255100 | A1* | 11/2007 | Barlow | A61B 1/0005 600/114 |
| 2007/0270651 | A1* | 11/2007 | Gilad | A61B 1/00147 600/160 |
| 2008/0108869 | A1* | 5/2008 | Sanders | A61B 1/00105 600/109 |
| 2008/0269779 | A1* | 10/2008 | Cadeddu | A61B 17/0469 606/130 |
| 2010/0076259 | A1* | 3/2010 | Asada | A61B 1/00096 600/102 |
| 2010/0081875 | A1* | 4/2010 | Fowler | A61B 1/00149 600/114 |
| 2010/0225753 | A1* | 9/2010 | Karasawa | A61B 1/041 348/65 |
| 2010/0249512 | A1* | 9/2010 | McKinley | A61B 17/3421 600/160 |
| 2010/0261961 | A1* | 10/2010 | Scott | A61B 1/00193 600/111 |
| 2011/0046445 | A1* | 2/2011 | Asada | A61B 1/041 600/158 |
| 2011/0071473 | A1* | 3/2011 | Rogers | A61B 1/00149 604/167.01 |
| 2012/0245416 | A1* | 9/2012 | Viola | A61B 1/0008 600/109 |
| 2013/0006052 | A1* | 1/2013 | Song | A61B 1/0008 600/109 |
| 2013/0096381 | A1* | 4/2013 | Manohara | A61B 1/00039 600/109 |
| 2014/0094655 | A1* | 4/2014 | Newman | A61B 1/0008 600/109 |
| 2015/0327750 | A1* | 11/2015 | Ogawa | A61B 1/00183 600/106 |

\* cited by examiner

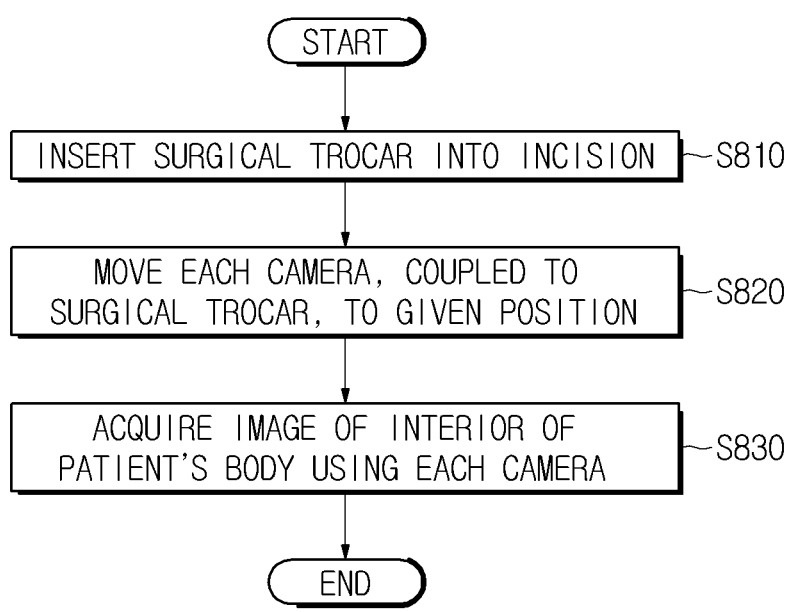

SURGICAL TROCARS AND IMAGE ACQUISITION METHOD USING THE SAME

CROSS-REFERENCE TO RELATED APPLICATION

This application claims the benefit of priority under 35 U.S.C. § 119 from Korean Patent Applications No. 10-2013-0049257, filed on May 2, 2013 in the Korean Intellectual Property Office, the disclosure of which is incorporated herein by reference in its entirety.

BACKGROUND

1. Field

Example embodiments relate to surgical trocars to acquire an image of the entire abdominal cavity of a patient and/or an image acquisition method using the same.

2. Description of the Related Art

Minimally invasive surgery refers to surgical methods to minimize the size of an incision. Differently from laparotomy using a relatively large surgical incision through a part of a human body (e.g., the abdomen), in minimally invasive surgery, after forming at least one small port (or incision) of 0.5 cm-1.5 cm through the abdominal wall, an operator inserts an endoscope and a variety of surgical instruments through the port, to perform surgery while viewing an image.

As compared to laparotomy, minimally invasive surgery has several advantages, such as low pain after surgery, early recovery, early restoration of ability to eat, short hospitalization, rapid return to daily life, and superior cosmetic effects owing to a small incision. Accordingly, minimally invasive surgery has been used in gall resection, the treatment of prostate cancer, and herniotomy operations, etc., and the use range thereof increasingly expands.

In general, a surgical robot used in minimally invasive surgery includes a master device and a slave device. The master device generates a control signal corresponding to doctor manipulation to transmit the control signal to the slave device. The slave device receives the control signal from the master device to perform manipulation required for surgery of a patient. The master device and the slave device may be integrated with each other, or may be separately arranged in an operating room.

Examples of surgical robots include a multi-port surgical robot that forms a plurality of incisions in the body of a patient to insert a plurality of surgical instruments through the respective incisions in a one-to-one ratio, and a single-port surgical robot that forms a single incision in the body of the patient to insert a plurality of surgical instruments through the single incision at once. Here, the single-port surgical robot forms a single incision differently from the multi-port surgical robot and has been in the limelight owing to advantages of the narrow incision and early recovery.

To safely put or pull the surgical instruments into or out of the single incision or the plurality of incisions, a trocar is installed per incision such that the surgical instruments are put into or pull out of the patient's body through the trocar.

SUMMARY

Example embodiments provide surgical trocars that may easily acquire an image of the entire abdominal cavity and/or an image acquisition method using the same.

In accordance with example embodiments, a surgical trocar includes a body having a passage configured to receive at least one surgical instrument, and at least one camera movably coupled to an outer wall of the body.

The surgical trocar may further include a first link having a first end provided with the at least one camera and a second end, and a first joint connecting the second end of the first link and an outer wall of the body to each other. The first link may be configured to move as the first joint is rotated.

The second end of the first link may include a first coupling portion connected to the outer wall of the body via the first joint, and a second coupling portion separated from the first coupling portion.

The surgical trocar may further include a second link having a first end connected to the second coupling portion of the first link, and a second end protruding outward from the body in a longitudinal direction of the passage. The surgical trocar may further include a third link having a first end connected to the outer wall of the body, and a second end connected to the second link. The surgical trocar may further include a second joint connecting the first end of the second link and the second coupling portion provided at the second end of the first link to each other, a third joint connecting the first end of the third link and the outer wall of the body to each other, and a fourth joint connecting the second end of the third link and the second link to each other.

The surgical trocar may further include a groove in the outer wall of the body, the groove extending in a longitudinal direction of the passage. The second end of the first link, the first end of the second link, and the third link may be inserted into the groove.

The second end of the first link, the first end of the second link, and the third link may be configured not to extend beyond the outer wall of the body when inserting the surgical trocar in an incision of a patient.

The second end of the first link, the first end of the second link, and the third link may be configured to be planar with the outer wall of the body when inserting the surgical trocar in an incision of a patient.

The second coupling portion of the first link connected to the first end of the second link may be configured to move in a pulling direction of the second link if the second end of the outwardly protruding second link is pulled. The first link may be configured to move as the first joint is rotated via movement of the second coupling portion.

The surgical trocar may further include a groove in the outer wall of the body to have a set length in a peripheral direction, wherein the first link and the camera are configured to be inserted into the groove.

The surgical trocar may further include a drive unit provided at the first joint to rotate the first joint.

The first link and the at least one camera may be configured to be inserted into the groove or protrude outward according to rotation of the first joint.

The drive unit may include a motor.

The first link may be configured to be planar with the outer wall of the body when inserting the surgical trocar in an incision of a patient.

The first link may be configured not to extend beyond the outer wall of the body when inserting the surgical trocar in an incision of a patient.

In accordance with other example embodiments, in an image acquisition method using a surgical trocar including a main body having a passage configured to receive at least one surgical instrument, the method includes inserting the surgical trocar into an incision formed in a body of a patient, moving at least one camera movably coupled to an outer wall of the main body to a given position, and acquiring at least one image of an interior of the body of the patient.

The inserting of the surgical trocar may include inserting the at least one camera inside the body of the patient.

The moving of the at least camera to the given position may be performed by a user moving a link of the main body, or by using a drive motor operatively connected to the surgical trocar.

The at least one camera may include a plurality of cameras configured to each be moved to different positions respectively.

The method may further include, after the acquiring of the at least one image, matching a plurality images of the at least one image to one another to form a final image.

The formation of the final image may include extracting at least one feature from respective images of the plurality of images, estimating homography between the respective images using the extracted features, and matching the respective images to one another using the estimated homography.

BRIEF DESCRIPTION OF THE DRAWINGS

Example embodiments will be more clearly understood from the following detailed description taken in conjunction with the accompanying drawings. FIGS. 1-8 represent non-limiting, example embodiments as described herein.

FIG. 1 is a view showing an outer appearance of a surgical robot;

FIG. 2 is a view showing a state in which surgical instruments are inserted through a trocar;

FIG. 3 is a view showing a configuration of the surgical trocar, to which a camera is coupled, according to example embodiments;

FIG. 4 is a sectional view taken along the line A-A' of FIG. 3;

FIG. 6 is a plan view showing a configuration of the surgical trocar, to which a camera is coupled, according to example embodiments;

FIG. 8 is a flowchart showing the sequence of an image acquisition method using the surgical trocar to which the camera is coupled.

DETAILED DESCRIPTION

Figure 1:
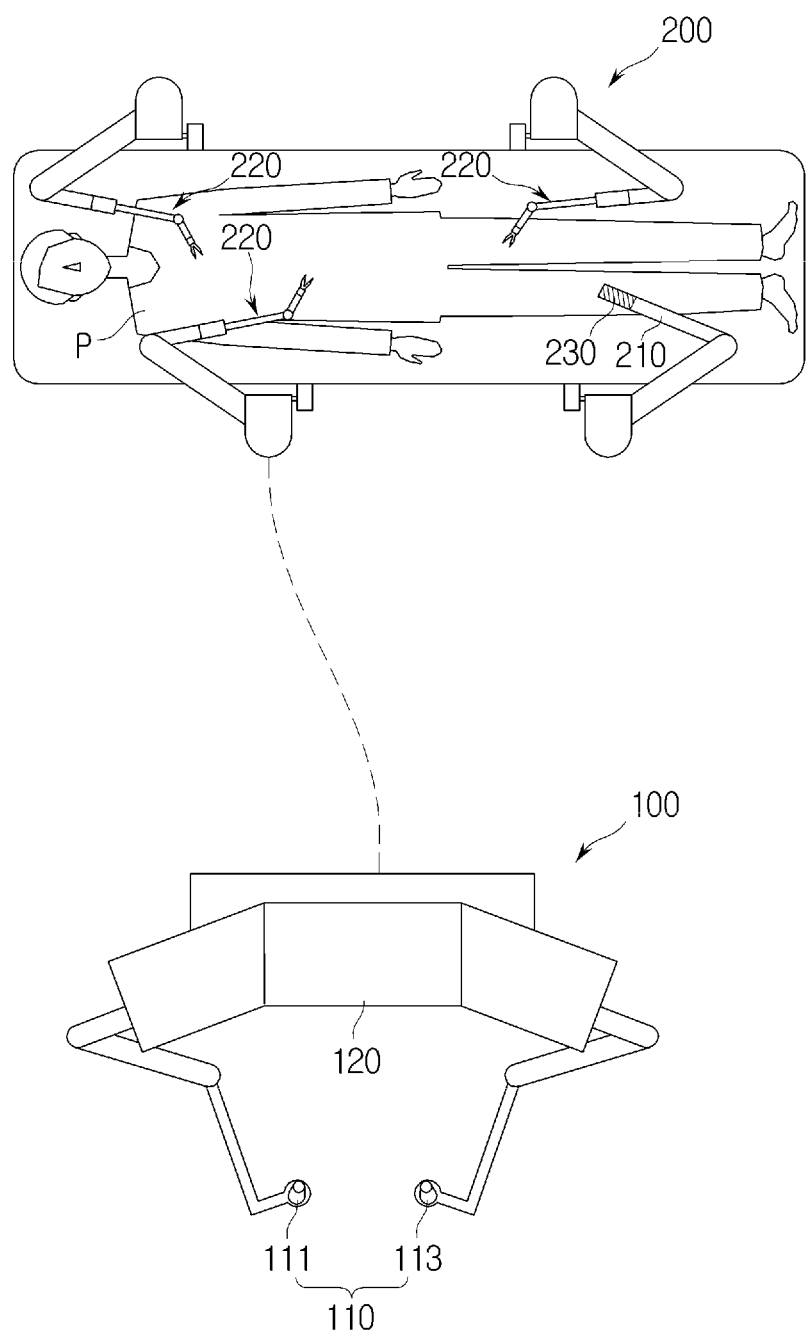

Various example embodiments will now be described more fully with reference to the accompanying drawings in which some example embodiments are shown. However, specific structural and functional details disclosed herein are merely representative for purposes of describing example embodiments. Thus, the invention may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In order to more specifically describe example embodiments, various features will be described in detail with reference to the attached drawings. However, example embodiments described are not limited thereto.

Hereinafter, reference will now be made in detail to the embodiments of the present invention, examples of which are illustrated in the accompanying drawings, wherein like reference numerals refer to like elements throughout.

Figure 2:
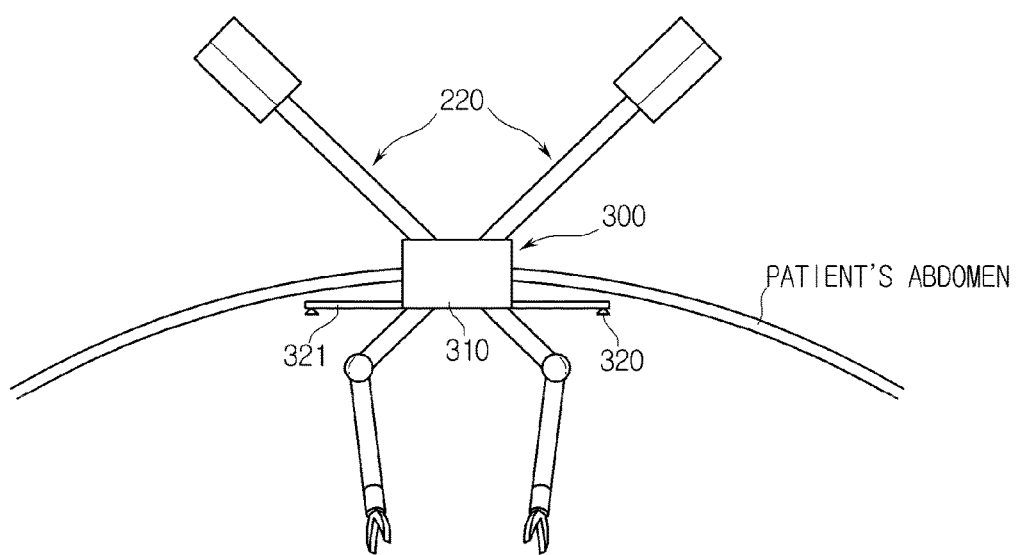

FIG. 1 is a view showing an outer appearance of a surgical robot, and FIG. 2 is a view showing a state in which surgical instruments are inserted through a trocar.

Referring to FIG. 1, a surgical robot may include a slave device 200 to perform surgery on a patient P who lies on an operating table, and a master device 100 to assist an operator (e.g., a doctor) in remotely controlling the slave device 200. In this case, at least one assistant who assists the operator may be located near the patient P.

Here, assisting the operator may mean assisting surgery by the operator in a real space where the patient P is located. This assistance may include a change of used surgical instruments, without being in any way limited thereto. For example, various surgical instruments may be used according to the kind of surgery and the number of robot arms 210 of the slave device 200, and consequently the number of surgical instruments used at once may be limited.

Accordingly, to change surgical instruments during surgery, the operator may instruct an assistant near the patient P to change surgical instruments, and the assistant may change surgical instruments according to the operator's instruction by pulling out the surgical instruments inserted in the abdominal cavity of the patient P to replace the used surgical instruments and inserting other surgical instruments.

The master device 100 and the slave device 200 may be physically separate devices, without being in any way limited thereto. In example embodiments, the master device 100 and the slave device 200 may be integrated with each other.

As exemplarily shown in FIG. 1, the master device 100 may include an input unit 110 and a display unit 120.

The input unit 110 may receive an instruction input by the operator, such as, for example, an instruction for selection of an operation mode of the surgical robot, or an instruction for remote control of motion of robot arms 210, surgical instruments 220, and an image capture unit 230 of the slave device 200. The input unit 110 according to the present example embodiments may include a haptic device, clutch pedal, switch, button, or the like, without being in any way limited thereto. In example embodiments, a voice recognition device may be used. It will be clearly understood that the haptic device will be described hereinafter as an example of the input unit 110, but the aforementioned various other devices may be used as the input unit 110.

Although FIG. 1 shows the input unit 110 as including two handles 111 and 113, the disclosure is not limited thereto. For example, the input unit 110 may include one handle, or three or more handles.

The operator may control motion of the robot arms 210 and surgical instruments 220 of the slave device 200 by moving the two handles 111 and 113 with both hands. That is, if the operator manipulates the input unit 110, the master device 100 may generate a control signal corresponding to information regarding the state of the manipulated input unit 110 to transmit the control signal to the slave device 200, and the slave device 200 may operate the robot arms 210 and the surgical instruments 220 in response to the transmitted control signal.

The display unit 120 of the master device 100 may display, e.g., an image of a surgical region inside the patient's body collected by the endoscope 230 of the slave device 200 as well as a 3D virtual image generated using medical images of the patient before surgery. In the present example embodiments, additionally, the display unit 120 may display a real image of the entire interior of the patient's body collected via a camera 320 coupled to a surgical trocar 300 that will be described hereinafter.

To this end, the master device 100 may include an image processor (not shown) that receives and processes image data transmitted from the slave device 200 to output the processed data to the display unit 120. As described above, the "image data" may include an image of a surgical region collected via the endoscope 230, a 3D virtual image generated using medical images of the patient before surgery, and a real image of the entire interior of the patient's body collected via the camera 320 coupled to the surgical trocar 300, without being in any way limited thereto.

The display unit 120 may include one or more monitors such that the respective monitors individually display information required for surgery. In example embodiments, if the display unit 120 includes three monitors, one of the monitors may display, e.g., an image of a surgical region collected via the endoscope 230 and a 3D virtual image generated using medical images of the patient before surgery, another monitor may display a real image of the entire interior of the patient's body collected via the camera 320 coupled to the surgical trocar 300, and the other monitor may display e.g., information regarding motion of the slave device 200 and patient information. In another example, a plurality of monitors may display the same image. In this case, the respective monitors may display the same image, or a single image may be displayed on all of the plurality of monitors. In addition, the number of monitors may be determined in various ways according to the type or kind of information to be displayed. The aforementioned display unit 120, for example, may be a Liquid Crystal Display (LCD) unit or a Light Emitting Diode (LED) unit, without being in any way limited thereto.

Here, "patient information" may be information regarding the state of the patient, for example, patient vital signs, such as body-temperature, pulse, respiration-rate, blood-pressure, etc. To provide the master device 100 with the vital signs, the slave device 200 that will be described hereinafter may further include a vital sign measurement unit including a body-temperature measurement module, a pulse measurement module, a respiration-rate measurement module, a blood-pressure measurement module, etc. To this end, the master device 100 may further include a signal processor (not shown) that receives and processes information transmitted from the slave device 200 to output the processed information to the display unit 120.

The slave device 200 may include a plurality of robot arms 210, and surgical instruments 220 mounted at ends of the respective robot arms 210. In addition, as exemplarily shown in FIG. 2, the slave device 200 may further include the surgical trocar 300 inserted into an incision formed in the body (e.g., the abdomen) of the patient P, the surgical trocar 300 serving to assist the operator in safely putting or pulling the surgical instruments 220 into or out of the patient's body. In this case, although FIG. 2 shows the surgical trocar 300 into which a plurality of surgical instruments 220 is inserted, one surgical instrument 220 may naturally be inserted into the single surgical trocar 300.

Although not shown in detail in FIG. 1, each of the plurality of robot arms 210 may include a plurality of links and a plurality of joints. Each joint may serve to connect two links to each other, and may have 1 degree of freedom (DOF) or more. The DOF refers to a DOF with regard to kinematics or inverse kinematics. The DOF of a mechanism refers to the number of independent motions of the mechanism, or the number of variables that determine independent motions at relative positions between links. For example, an object in a 3D space defined by X-, Y-, and Z-axes has 3 DOF to determine a spatial position of the object (a position on each axis) and/or 3 DOF to determine a spatial orientation of the object (a rotation angle relative to each axis). More specifically, it will be appreciated that an object has 6 DOF if the object is movable along each of X-, Y-, and Z-axes and is rotatable about each of X-, Y-, and Z-axes.

Although not shown in detail in FIG. 1, the surgical instrument 220 may include a housing mounted to the end of the robot arm 210, a shaft extending from the housing by a set (or, predetermined) length, and an end effector coupled to a distal end of the shaft.

In general, the surgical instruments 220 may be basically classified into main surgical instruments and auxiliary surgical instruments. Here, the "main surgical instrument" may refer to an instrument including an end effector (e.g., a knife or a surgical needle) that performs direct surgical motion, such as, e.g., cutting, suturing, clotting, or washing, on a surgical region. The "auxiliary surgical instrument" may refer to an instrument including an end effector (e.g., a skin holder) that does not perform direct motion on a surgical region and assists motion of the main surgical instrument.

The end effector is a part of the surgical instrument 220 that practically acts on a surgical region of the patient P. For example, the end effector may include a skin holder, suction line, knife, scissors, grasper, surgical needle, staple applier, needle holder, scalpel, cutting blade, etc., without being in any way limited thereto. Any other known instruments required for surgery may be used.

A drive wheel may be coupled to the housing and connected to the end effector via a wire, etc. Thus, the end effector may be operated via rotation of the drive wheel. To this end, a drive unit (not shown) to rotate the drive wheel may be provided at the end of the robot arm 210. For example, if the operator manipulates the input unit 110 of the master device 100, the master device 100 generates a control signal corresponding to information regarding the state of the manipulated input unit 110 to transmit the control signal to the slave device 200. As the slave device 200 drives the drive unit (not shown) in response to the transmitted control signal, desired motion of the end effector may be realized. However, a mechanism to operate the end effector is not limited to the aforementioned configuration and various electrical/mechanical mechanisms may naturally be applied to realize motion of the end effector required for robotic surgery.

The endoscope 230 of the slave device 200 serves to assist motion of a main surgical instrument rather than directly performing surgical motion on a surgical region. Thus, it will be appreciated that the endoscope 230 corresponds to an auxiliary surgical instrument in a broad sense. The endoscope 230 may be selected from among various surgical endoscopes, such as a thoracoscope, arthroscope, rhinoscope, cystoscope, proctoscope, duodenoscope, and cardioscope, in addition to a celioscope that is mainly used in robotic surgery.

In addition, the endoscope 230 may be a Complementary Metal Oxide Semiconductor (CMOS) camera or a Charge Coupled Device (CCD) camera, without being in any way limited thereto. The endoscope 230 may include a lighting device (not shown) to emit light to a surgical region. In addition, the slave device 200 may further include a display unit (not shown) to display a real image of the interior of the patient's body collected via the endoscope 230.

The surgical trocar 300 according to the present example embodiments, as exemplarily shown in FIG. 2, may basically include a body 310 having a passage for insertion of the surgical instruments 220, and the camera 320 movably coupled to an outer wall of the body 310. In this case, links and joints may be used to movably couple the camera 320 to the outer wall of the body 310. Although example embodiments to realize the aforementioned configuration using the links and joints will be described hereinafter with reference to the drawings, these example embodiments are given by way of example and a connection configuration between the camera 320 and the body 310 is not in any way limited to the following description and various other movable coupling configurations may be within the scope of the example embodiments.

First, a configuration of the surgical trocar according to example embodiments will be described with reference to FIGS. 3 to 5.

Figure 3:
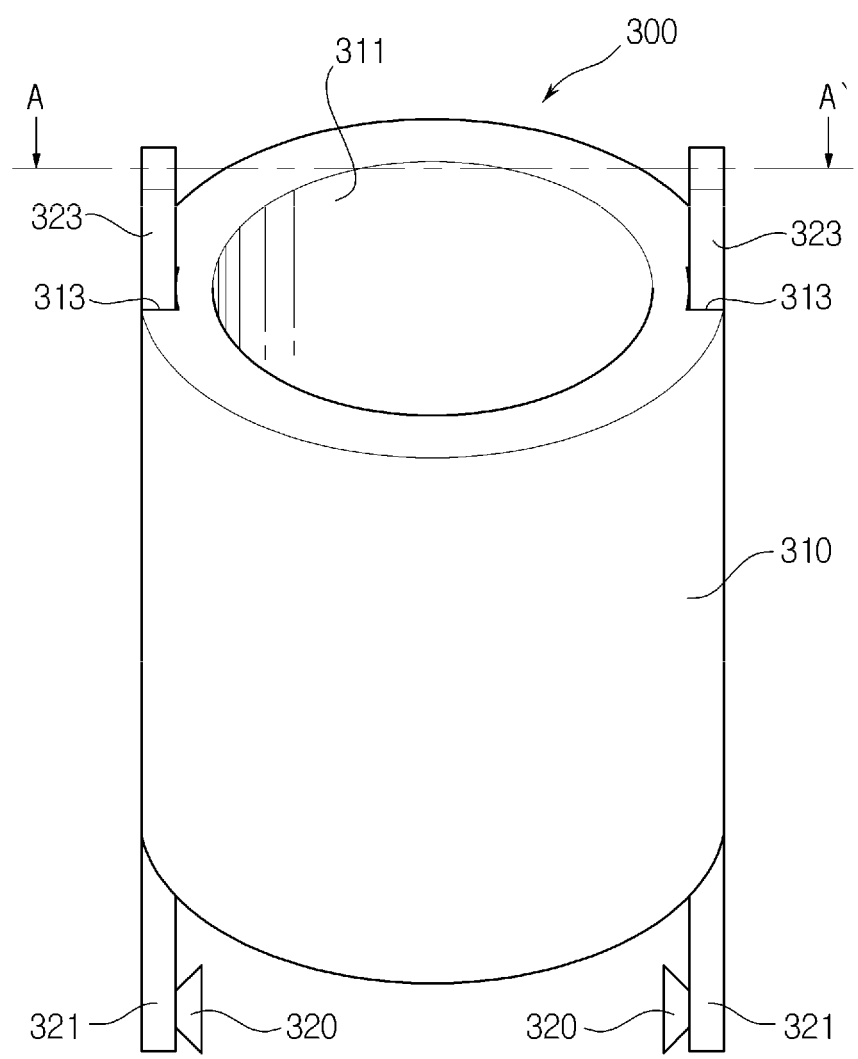
Figure 4:
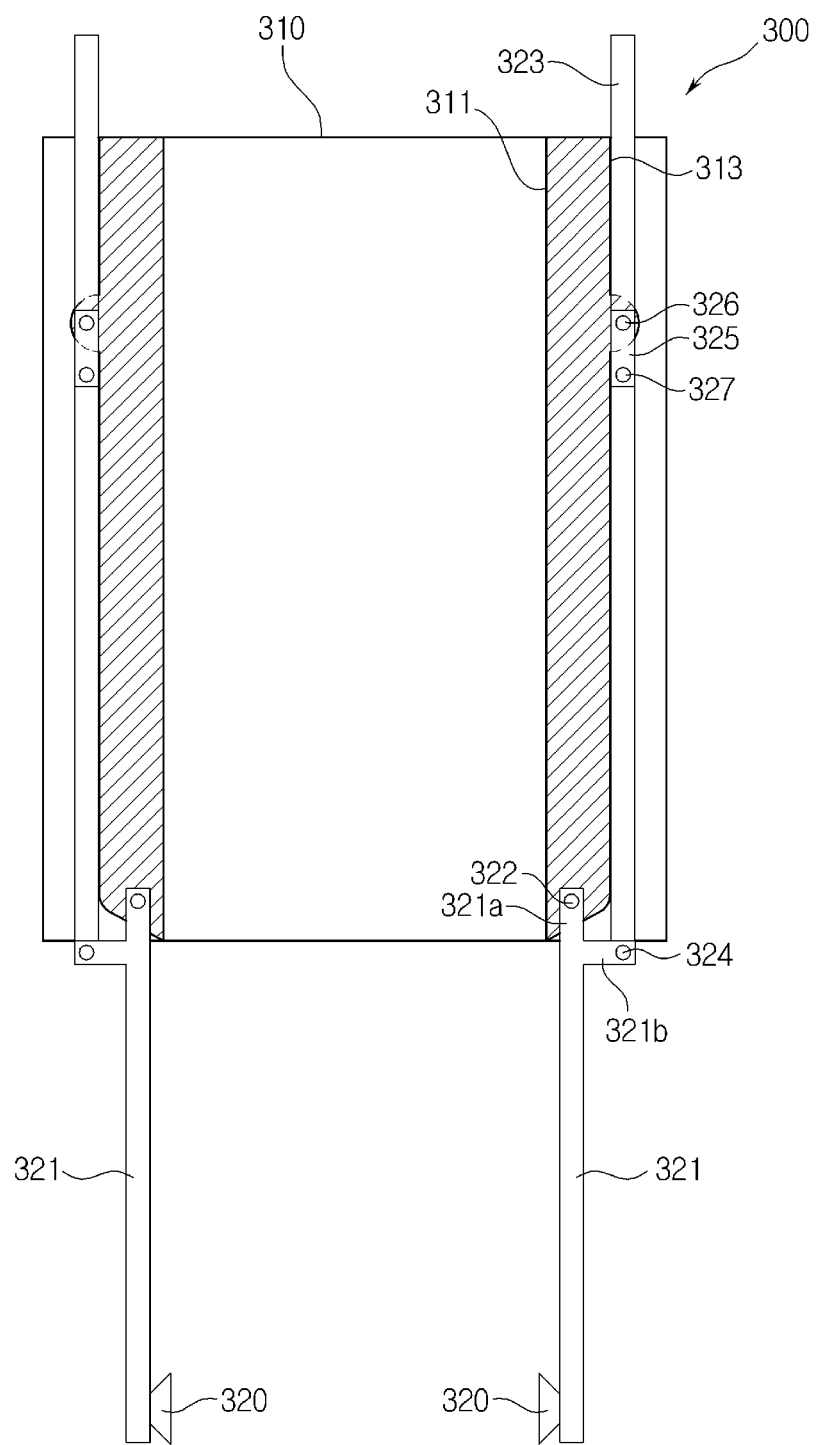

FIG. 3 is a view showing an outer appearance of the surgical trocar according to example embodiments, FIG. 4 is a sectional view taken along the line A-A' of FIG. 3, and FIGS. 5A, 5B and 5C are views showing movement of the camera coupled to the surgical trocar of FIG. 3.

Referring to FIGS. 3 and 4, a surgical trocar 300 according to the present example embodiments may include the body 310 having a passage 311 for insertion of the surgical instruments 220, and the camera 320 movably coupled to an outer wall of the body 310. In the present example embodiments, the camera 320 may be coupled to the outer wall of the body 310 using a plurality of links 321, 323 and 325 and a plurality of joints 322, 324, 326 and 327. That is, in the present example embodiments, if the operator pulls out one outwardly protruding link 323 among the plurality of links 321, 323 and 325, the respective joints 322, 324, 326 and 327 are rotated, causing movement of the camera 320. Meanwhile, although FIGS. 3 and 4 show the surgical trocar 300 as including two cameras 320, the number of cameras 320 that may be coupled to the body 310 is not in any way limited.

More specifically, the surgical trocar 300 according to the present example embodiments, as exemplarily shown in FIGS. 3 and 4, may include a first link 321, a second link 323, a third link 325, a first joint 322, a second joint 324, a third joint 326 and a fourth joint 327. One end of the first link 321 is coupled to the camera 320, and the other end of the first link 321 is divided into a first coupling portion 321a connected to the outer wall of the body 310 and a second coupling portion 321b. One end of the second link 323 is connected to the second coupling portion 321b of the first link 321, and the other end of the second link 323 protrudes outward. One end of the third link 325 is connected to the outer wall of the body 310, and the other end of the third link 325 is connected to the second link 323. The first joint 322 connects the first coupling portion 321a of the first link 321 and the outer wall of the body 310 to each other. The second joint 324 connects one end of the second link 323 and the second coupling portion 321b of the first link 321 to each other. The third joint 326 connects one end of the third link 325 and the outer wall of the body 310 to each other. The fourth joint 327 connects the other end of the third link 325 and the second link 323 to each other.

In this case, the first link 321, the second link 323 and the third link 325 may initially have a rectilinear arrangement as exemplarily shown in FIG. 4. One end of the first link 321, to which the camera 320 is mounted, may protrude from the bottom of the body 310. The other end of the second link 323 may protrude from the top of the body 310, but the disclosure is not limited thereto. This configuration may prevent patient injury when the surgical trocar 300 is inserted into the incision. Here, the "bottom of the body 310" and the "top of the body 310" may respectively refer to a portion located inside the patient's body and a portion located outside the patient's body, respectively, when the surgical trocar 300 is inserted into the incision.

With the aforementioned connection configuration, the first coupling portion 321a of the first link 321 and one end of the third link 325 are connected to the outer wall of the body 310. Thus, the links 321 and 325 are only rotatable while remaining in position. As a connection region between the second coupling portion 321b of the first link 321 and one end of the second link 323, and a connection region between the second link 323 and the other end of the third link 325, are respectively rotated and moved about the fixed positions of the first link 321 and the third link 325, a position of the camera 320 may be moved.

Figure 5A:
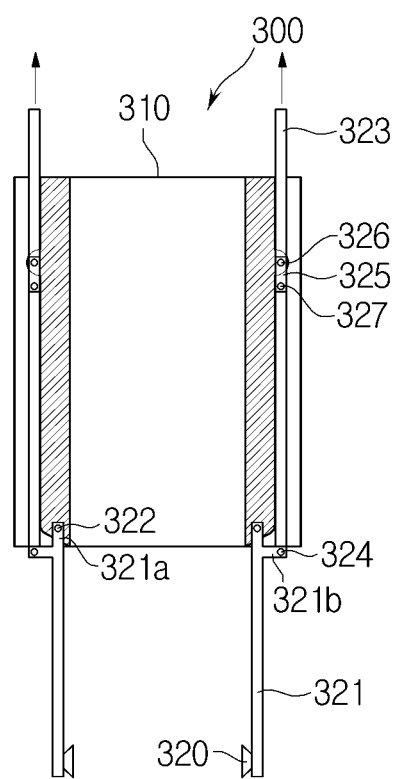
FIGS. 5A, 5B and 5C are views showing movement of the camera coupled to the surgical trocar of FIG. 3.
Figure 5B:
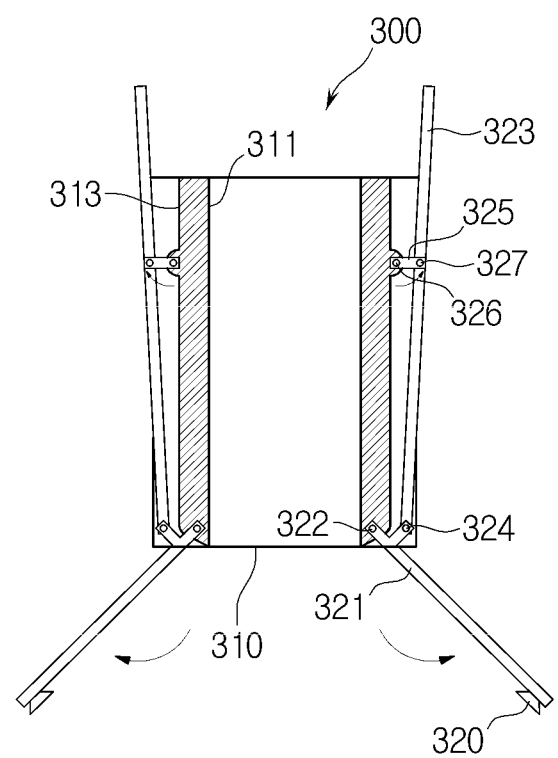
Figure 5C:
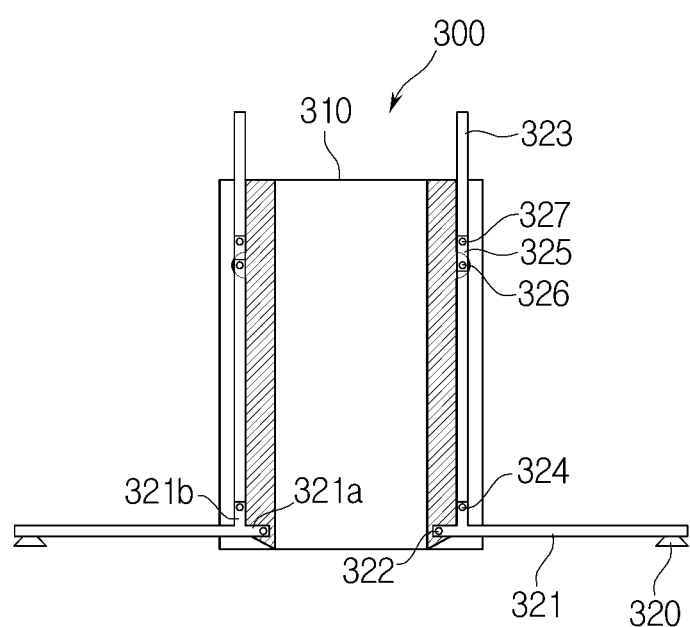

That is, if the other end of the outwardly protruding second link 323 is pulled in a direction designated by the arrow in an initial arrangement state of the respective links as exemplarily shown in FIG. 5A, one end of the third link 325 coupled to the outer wall of the body 310 is rotated in position, the other end of the third link 325 connected to the second link 323 moved in the same direction as the pulling direction of the second link 323 while being rotated in a direction designated by the arrow, the first coupling portion 321a of the first link 321 coupled to the outer wall of the body 310 is rotated in position, and the second coupling portion 321b of the first link 321 connected to the second link 323 is rotated and moved in the pulling direction of the second link 323, as shown in FIG. 5B. As such, the first link 321 is moved in a direction designated by the arrow. FIG. 5C shows a completely moved state of the first link 321.

In this way, the surgical trocar 300 according to the present example embodiments is configured such that the camera 320 is coupled to the body 310 using the plurality of links 321, 323 and 325 and the plurality of joints 332, 324, 326 and 327 and may be moved as the outwardly protruding link 323 among the plurality of links 321, 323 and 325 is manually pulled. That is, once the surgical trocar 300 has been inserted into the incision in a state in which the first link 321 to which the camera 320 is mounted is linearly aligned with the outer wall of the body 310, the outwardly protruding second link 323 may be pulled to move the first link 321, which enables the camera 320 to be arranged at a given position. However, instead of manually moving the camera 320, automated movement of the camera 320 may be realized as a drive unit is mounted to each of the joints 322, 324, 326 and 327 to rotate the corresponding joint 322, 324, 326 or 327.

The surgical trocar 300 according to the present example embodiments may further include a groove 313 formed in the outer wall of the body 310 to extend in a longitudinal direction of the passage 311. The first coupling portion 321a of the first link 321 and one end of the third link 325 may be coupled to an inner wall of the groove 313 and the first, second and third links 321, 323 and 325 may be inserted into the groove 313, although the disclosure is not in any way limited thereto. Inserting all of the links into the groove 313 may ensure safe insertion of the surgical trocar 300 into the incision without causing injury of the abdomen of the patient P. In this case, a coupling protrusion (not shown) may be formed at the inner wall of the groove 313 to ensure easy connection between the first coupling portion 321a of the first link 321 and one end of the third link 325.

Next, a configuration of the surgical trocar according to other example embodiments will be described with reference to FIGS. 6 and 7. Here, the same components as those of the surgical trocar 300 according to the above-described example embodiments will be designated by the like reference numerals.

Figure 6:
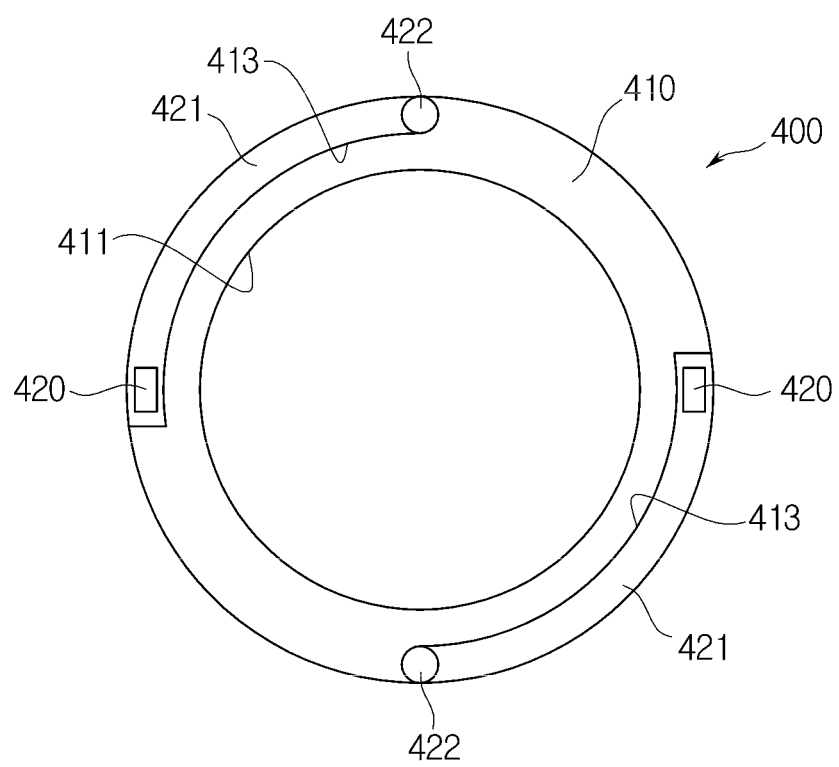
Figure 7A:
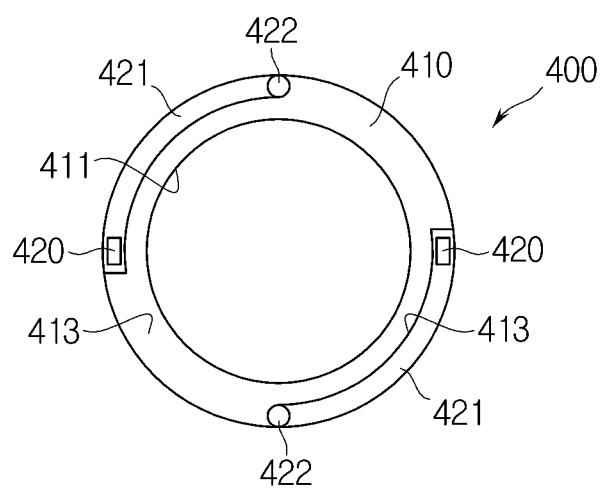
FIGS. 7A and 7B are plan views showing movement of the camera coupled to the surgical trocar of FIG. 6.
Figure 7B:
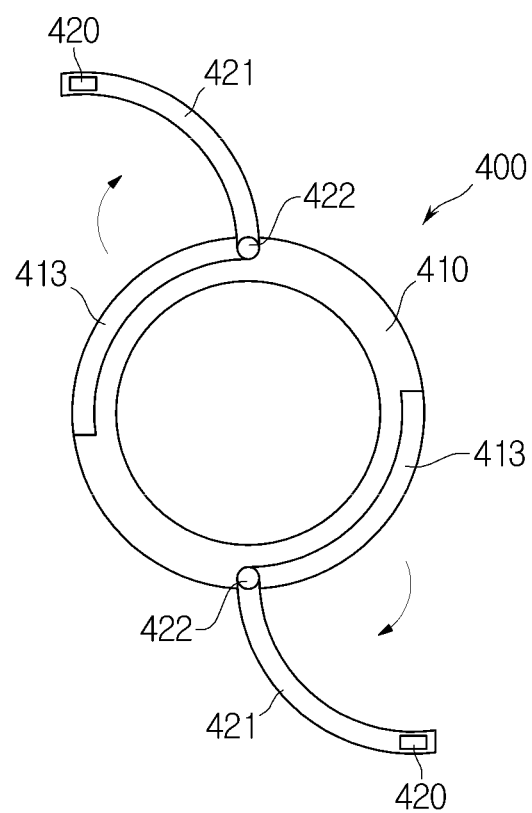

FIG. 6 is a bottom plan view showing a configuration of the surgical trocar according to other example embodiments, and FIGS. 7A and 7B are plan views showing movement of the camera coupled to the surgical trocar of FIG. 6.

Referring to FIG. 6, a surgical trocar 400 according to the present example embodiments may include the body 410 having the passage 411 for insertion of the surgical instruments 220, and the camera 420 movably coupled to the outer wall of the body 410. In the present example embodiments, the camera 420 may be coupled to the outer wall of the body 410 using one link 421 and one joint 422.

More specifically, the surgical trocar 400 according to the present example embodiments, as exemplarily shown in FIG. 6, may include the first link 421, and a first joint 422. One end of the first link 421 is coupled to the camera 420, and the other end of the first link 421 is connected to the outer wall of the body 410. The first joint 422 connects the other end of the first link 421 and the outer wall of the body 410 to each other. In this case, the first link 421 may have a shape corresponding to the periphery of the body 410 and the groove 413 may be formed in the outer wall of the body 410 such that a peripheral length of the groove 413 is equal to a length of the first link 421, although the disclosure is not in any way limited thereto. With this configuration, as exemplarily shown in FIG. 6, the first link 421 may be inserted into the groove 413. This enables installation of the camera 420 without deformation of the outer wall of the body 410 of the surgical trocar 400.

That is, once the surgical trocar 400 has been inserted into the incision in a state in which the first link 421 is inserted in the groove 413 as exemplarily shown in FIG. 7A, the first joint 422 is rotated to move the first link 421 in a direction designated by the arrow as exemplarily shown in FIG. 7B, which enables the camera 420 to be arranged at a given position. In this case, a drive unit (not shown) to rotate the first joint 422 may be provided at the first joint 422. Here, the "drive unit" may be a motor, for example, without being in any way limited thereto.

The aforementioned motor may be driven upon receiving a signal transmitted from a controller (not shown) of the slave device 200. For example, to move the camera 420 coupled to the surgical trocar 400 to a given position after the surgical trocar 400 is inserted into the incision formed in the abdomen of the patient P, if the operator manipulates the input unit 110 of the master device 100 and a controller (not shown) of the master device 100 generates a control signal corresponding to the state of the manipulated input unit 110 to transmit the control signal to the slave device 200, the slave device 200 applies a signal required to rotate the first joint 422 to the aforementioned motor according to the transmitted control signal, thereby moving the first link 421 to which the camera 420 is mounted.

Although FIGS. 6, 7A and 7B show the surgical trocar 400 as including two cameras 420, the number of cameras 420 that may be coupled to the body 410 is not in any way limited. In addition, although FIG. 6 shows the body 410 as having a circular periphery and the first link 421 as having a curvilinear shape, the shape of the periphery of the body 410 is not in any way limited thereto and the first link 421 may have a shape corresponding to the shape of the periphery of the body 410.

FIG. 8 is a flowchart showing the sequence of an image acquisition method using the surgical trocar according to example embodiment.

First, referring to FIGS. 5A, 5B, 5C, 7A, 7B and 8, the surgical trocar 300 is inserted into the incision formed in the body (e.g., the abdomen) of the patient P (S810). In this case, the camera 320 has been coupled to the surgical trocar 300 inserted into the incision, and the surgical trocar 300 may be inserted into the incision such that the camera 320 is located inside the body of the patient P.

Next, the camera 320 coupled to the surgical trocar 300 inserted into the incision is moved to a given position (S820). In this case, moving the camera 320 to the given position may be manually or automatically implemented.

For example, as exemplarily shown in FIGS. 5A, 5B and 5C, the camera 320 may be manually moved as the outwardly protruding second link 323, connected to the first link 321 to which the camera 320 is mounted, is pulled in a direction designated by the arrow. In this case, the second link 323 may be pulled by the assistant located near the patient P, without being in any way limited thereto.

In addition, as exemplarily shown in FIGS. 7A and 7B, the camera 420 may be automatically moved as the first link 421, to which the camera 420 is mounted, is moved in a direction designated by the arrow via rotation of the first joint 422. In this case, the first joint 422 may be rotated by a drive unit (e.g., a motor) additionally provided at the first joint 422. That is, if the operator manipulates the input unit 110 and the master device 100 generates a signal to move the camera 420 coupled to the surgical trocar 400 according to manipulation of the operator to transmit the signal to the slave device 200, the slave device 200 drives the drive unit provided at the first joint 422 to rotate the first joint 422 in response to the transmitted signal, thereby moving the camera 420.

In this case, at least one camera 320 may be coupled to the surgical trocar 300. If a plurality of cameras 320 is provided, the cameras 320 may be moved to different positions. This serves to acquire an image of the entire interior of the patient's body.

Next, an image of the interior of the patient's body is acquired (S830).

In this case, if the plurality of cameras 320 is coupled to the surgical trocar 300 as described above, a plurality of images may be acquired (S830). Thus, it may be necessary to match the acquired images to one another, to acquire a single final image, i.e. an image of the entire interior of the patient's body. To generate a single image by matching a plurality of images acquired at different positions, a general matching method using feature extraction may be used. That is, after features are extracted from respective images, the extracted features are matched to one another to estimate homography between the images, and then the respective images are matched to one another using the estimated homography to acquire a single image. Here, homography estimation using the extracted features and image matching using the estimated homography are known technologies and deviate somewhat from the subject of the disclosure, and thus a detailed description thereof is omitted.

As described above, through provision of the surgical trocar 300 to which the plurality of cameras 320 is movably coupled, it may be possible to easily acquire an image of the entire abdominal cavity of the patient P and to acquire an image upon insertion of the surgical instruments 220, which enables safe and accurate surgery.

Although the example embodiments have been shown and described, it would be appreciated by those skilled in the art that changes may be made in these embodiments without departing from the principles and spirit of the invention, the scope of which is defined in the claims and their equivalents.

What is claimed is:

1. A surgical trocar, comprising:
    a body having a passage configured to receive at least one surgical instrument, the body being a cylinder that includes an outer wall having a groove therein along a circumference of the outer wall;
    at least one camera movably coupled to the outer wall of the body such that the at least one camera is configured to selectively extend outwardly from the groove based on rotation of a first joint within the groove, the first joint having a rotational axis parallel to a longitudinal axis of the body; and
    a first link having an arched shape corresponding to the circumference of the outer wall, the first link having a first end and a second end, a length of the first link between the first end and the second end being equal to a length of the groove, and the first end connected to the at least one camera and the second end connected to the first joint within the groove such that the first link is configured to extend from a closed state to an open state by rotating the first joint about the rotational axis parallel to the longitudinal axis of the body.

2. The surgical trocar according to claim 1,
    wherein the first link is configured to move as the first joint is rotated.

3. The surgical trocar according to claim 2, wherein the second end of the first link includes,
    a first coupling portion connected to the outer wall of the body via the first joint, and
    a second coupling portion separated from the first coupling portion.

4. The surgical trocar according to claim 3, further comprising:
    a second link having a first end connected to the second coupling portion of the first link, and a second end protruding outward from the body in a longitudinal direction of the passage;
    a third link having a first end connected to the outer wall of the body, and a second end connected to the second link;
    a second joint connecting the first end of the second link and the second coupling portion provided at the second end of the first link to each other;
    a third joint connecting the first end of the third link and the outer wall of the body to each other; and
    a fourth joint connecting the second end of the third link and the second link to each other.

5. The surgical trocar according to claim 4, further comprising:
    a groove in the outer wall of the body, the groove extending in a longitudinal direction of the passage, wherein the second end of the first link, the first end of the second link, and the third link are inserted into the groove.

6. The surgical trocar according to claim 4, wherein the second end of the first link, the first end of the second link, and the third link are configured not to extend beyond the outer wall of the body when inserting the surgical trocar in an incision of a patient.

7. The surgical trocar according to claim 4, wherein the second end of the first link, the first end of the second link, and the third link are configured to be planar with the outer wall of the body when inserting the surgical trocar in an incision of a patient.

8. The surgical trocar according to claim 4, wherein the second coupling portion of the first link connected to the first end of the second link is configured to move in a pulling direction of the second link if the second end of the outwardly protruding second link is pulled, and the first link is configured to move as the first joint is rotated via movement of the second coupling portion.

9. The surgical trocar according to claim 2, further comprising:

wherein the first link is configured to be inserted into the groove.

10. The surgical trocar according to claim 9, further comprising:

a drive unit provided at the first joint to rotate the first joint.

11. The surgical trocar according to claim 10, wherein the first link and the at least one camera are configured to be inserted into the groove or protrude outward according to rotation of the first joint.

12. The surgical trocar according to claim 10, wherein the drive unit includes a motor.

13. The surgical trocar of claim 2, wherein the first link is configured to be planar with the outer wall of the body when inserting the surgical trocar in an incision of a patient.

14. The surgical trocar of claim 2, wherein the first link is configured not to extend beyond the outer wall of the body when inserting the surgical trocar in an incision of a patient.

* * * * *